United States Patent [19]

Kampfer et al.

[11] Patent Number: 4,539,408
[45] Date of Patent: Sep. 3, 1985

[54] PROCESS FOR THE PREPARATION OF SULPHOALKYL QUATERNARY SALTS

[75] Inventors: Helmut Kampfer, Cologne; Marie Hase, Berg.-Gladbach; Max Glass, Cologne, all of Fed. Rep. of Germany

[73] Assignee: Agfa-Gevaert Aktiengesellschaft, Leverkusen, Fed. Rep. of Germany

[21] Appl. No.: 901,208

[22] Filed: Apr. 28, 1978

[30] Foreign Application Priority Data

Jan. 27, 1978 [DE] Fed. Rep. of Germany ..... 28034937

[51] Int. Cl.³ .................. C07D 293/12; C07D 285/00; C07D 277/00; C07D 263/00
[52] U.S. Cl. ..................................... 546/139; 544/338; 544/345; 546/141; 546/153; 546/157; 546/172; 546/339; 548/100; 548/121; 548/141; 548/142; 548/143; 548/150; 548/169; 548/178; 548/179; 548/186; 548/203; 548/217; 548/218; 548/219; 548/221; 548/230; 548/235; 548/329; 548/333; 548/337; 548/341; 548/551; 548/556; 548/565
[58] Field of Search ............... 260/298, 302 R, 302 S, 260/302 SD, 304 R, 304 C, 304 H, 306, 307 R, 307 C, 307 D, 307 F, 326.12 R, 326.12 S, 326.5 SF, 326.57, 326.9, 283 S, 286 Q, 294.8 S; 544/335, 345, 338; 546/139, 141, 172, 153, 157, 339; 548/100, 121, 120, 169, 179, 186, 178, 150, 143, 141, 142, 203, 217, 218, 219, 221, 229, 230, 235, 320, 329, 333, 337, 341, 551, 556, 565

[56] References Cited

U.S. PATENT DOCUMENTS

| 2,503,776 | 4/1950 | Sprague | 260/304 CX |
| 3,177,210 | 4/1965 | Rosenoff | 260/298 X |
| 3,274,204 | 9/1966 | Klass et al. | 260/294.8 S |
| 3,882,120 | 5/1975 | Piesch et al. | 548/320 X |
| 4,212,709 | 7/1980 | Patsch et al. | 204/49 |

Primary Examiner—Donald G. Daus
Assistant Examiner—Diana G. Rivers
Attorney, Agent, or Firm—Connolly and Hutz

[57] ABSTRACT

Quaternary sulfoalkyl or sulfoalkenyl salts of tertiary amine bases are prepared by reacting the tertiary amine bases at elevated temperatures with a hydroxy alkane sulfonic acid or a hydroxyalkene sulphonic acid.

7 Claims, No Drawings

PROCESS FOR THE PREPARATION OF SULPHOALKYL QUATERNARY SALTS

This invention relates to a process for the preparation of sulfoalkyl quaternary salts of tertiary amines, in particular of nitrogen-containing heterocyclic bases.

These quaternary salts, which contain positively and negatively charged groups joined together by covalent bonds, are also known as betaines. They play an important part in many commercial processes, in which they are either used as such, for example in electroplating work, or serve as intermediate products for further reactions. When sulfoalkyl betaines are used as intermediate products, it is frequently advantageous for commercial reasons not to isolate them first but to carry out the further reaction immediately after their preparation, in a single operation. As intermediate products, sulphoalkylbetaines are important, for example, for the synthesis of polymethine dyes which are used as spectral sensitizers for light-sensitive materials, in particular for photographic silver halide emulsions. To this extent, the present invention also relates to the conversion of the heterocyclic bases to polymethine dyes by way of the sulfoalkyl quaternary salts.

Processes for the preparation of sulfoalkyl quaternary salts of tertiary amines have been known for a long time. The tertiary bases are reacted with a sulfoalkylating agent, generally at elevated temperatures. Compounds which have been described as sulfoalkylating agents include the halogen alkane sulfonic acids such as 2-bromoethane sulphonic acid described in U.S. Pat. No. 2,503,776; sodium iodoethane sulfonate described in Belgian Pat. No. 669,308; sodium iodobutane sulfonate described in U.S. Pat. No. 2,912,329 and 3-chloro-2-hydroxypropane sulfonic acid described in German Auslegeschrift No. 1,177,482. Disadvantages of these sulfoalkylating agents are the high reaction temperatures required and the excess of tertiary base which is required when free sulfonic acids are used to take up the hydrogen halide formed in the reaction. Sultones are also known as sulfoalkylating agents, for example propane-, butane- and isopentane-sultone have been described in German Pat. No. 929,080; propanesultone in German Auslegeschrift No. 1,447,579 and 2-chloropropane sultone in British Pat. No. 1,090,626. One disadvantage of sultones is that in some cases they have a considerable carcinogenic potential which makes them dangerous to handle [see H. Druckrey et al Naturwiss. 55 (1968) 449; Z. Krebsforschung 75 (1970) 69].

An object of the present invention is therefore to provide a process for the preparation of sulfoalkyl and sulfalkenyl quaternary salts in which the disadvantages mentioned above would be reduced or substantially obviated.

A process for the preparation of a sulfoalkyl or sulfoalkenyl-quaternary salt of a tertiary amine has now been found in which the tertiary amine is reacted with a hydroxyalkane- or hydroxyalkenesulphonic acid. The reaction is generally carried out at an elevated temperature, e.g. at a temperature of from 100° C. to 250° C., preferably from 140° C. to 200° C.

The reaction generally proceeds quite smoothly within the last mentioned temperature range but temperatures outside this range may also be employed, depending to some extent on the nature of the solvent used, e.g. temperatures above 200° C., provided a higher boiling solvent is used as carrier for the water released by the reaction.

Suitable for use as tertiary amines are in principle any derivatives of ammonia (NH$_3$) in which all three hydrogen atoms are substituted, e.g. by a carbon atom of an alkyl or aryl group or by a carbon atom or a hetero atom of a heterocyclic ring, in which case the nitrogen atom of the tertiary amine, in particular, may be included in the heterocyclic ring. Particularly suitable heterocyclic bases are those corresponding to the following general formula I

in which

Z represents the members required to complete a heterocyclic group having at least one 5-membered or 6-membered heterocyclic ring; this hetero ring may contain condensed benzene, naphthalene or heterocyclic rings, which may in turn be substituted; the heterocyclic groups may be those known from the chemistry of cyanine dyes, e.g. the following:

Pyrroline (e.g. 4,4-dimethyl-pyrroline); oxazoline (e.g. 4,4-dimethyloxazoline); thiazoline (e.g. 5-methylthiazoline); selenazoline; indoline (e.g. 3,3-dimethylindoline, 3,3-dimethyl-5-methoxyindoline and 3,3-dimethyl-5-diethylaminoindoline); benzimidazole (e.g. 1-ethyl-5-trifluoromethyl-benzimidazole, 1-methyl-5-chlorobenzimidazole, 1-ethyl-5,6-dichlorobenzimidazole, 1-ethyl-5-cyanobenzimidazole, 1-methyl-5-carbethoxybenzimidazole, 1-ethyl-5-acetylbenzimidazole, 1-methyl-benzimidazole-5-sulfonic acid pyrrolidide, 1-ethylbenzimidazole-5-sulphonic acid dimethylamide, 1-ethyl-5-phenylthiobenzimidazole, 1-methyl-5-methylthiobenzimidazole and 1-methyl-5-chloro-6-methylthiobenzimidazole); oxazole (e.g. 4-methyloxazole, 4,5-diphenyloxazole, 4-methyl-5-carbethoxyoxazole, benzoxazole, 5-chlorobenzoxazole, 5-phenylbenzoxazole, 6-methoxybenzoxazole, 5-methoxybenzoxazole, 5-methyl-6-methoxybenzoxazole, 5-bromobenzoxazole, 5-iodobenzoxazole, naphtho[2,1-d]oxazole, naphtho[1,2-d]oxazole, naphtho[2,3-d]oxazole, 4,5,6,7-tetrahydrobenzoxazole and benzofuro[2,3-f]benzoxazole); thiazole (e.g. 4-methylthiazole, 4-phenylthiazole, 4-methyl-thiazole-5-acrylic acid ethyl ester, benzothiazole, 5-methylbenzothiazole, 6-methylbenzothiazole, 5-chlorobenzothiazole, 5-methoxy-benzothiazole, 6-methoxy-benzothiazole, 5,6-dimethyl-benzothiazole, 5,6-dimethoxy-benzothiazole, 5-methyl-6-methoxybenzothiazole, 5-bromobenzothiazole, 5-phenyl-benzothiazole, 6-methylthiobenzothiazole, 6-dimethylaminobenzothiazole, 5-chloro 6-methoxy-benzothiazole, 5,6-methylenedioxybenzothiazole, 6-β-cyanoethoxy-benzothiazole, 5-carbomethoxybenzothiazole, 5-nitrobenzothiazole, 5-phenylthiobenzothiazole, 5-thienylbenzothiazole, 6-hydroxybenzothiazole, 4,5,6,7-tetrahydro-benzothiazole, 4-oxo-4,5,6,7-tetrahydrobenzothiazole, naphtho[2,1-d]thiazole, naphtho[1,2-d]thiazole, 4,5-dihydronaphtho[1,2-d]thiazole, 5-methoxynaphtho[1,2-d]thiazole and 5,7,8-trimethoxynaphtho[1,2-d]thiazole);

selenazole (e.g. benzoselenazole, 5-methylbenzoselenazole, 5,6-dimethyl-benzoselenazole, 5-methoxybenzoselenazole, 5-methyl-6-methoxybenzoselenazole, 5,6-dimethoxy-benzoselenazole, 5,6-methylenedioxybenzoselenazole, 6-methyl-benzoselenazole and naphtho[1,2-d]selenazole); 1,3,4-oxadiazole (e.g. 5-methyl-1,3,4-oxadiazole, 5-phenyl-1,3,4-oxadiazole); 1,3,4-thiadiazole (e.g. 5-methyl-1,3,4-thiadiazole, 2,5-bis-methylthio-1,3,4-thiadiazole, 5-benzylthio-1,3,4-thiadiazole, 2-mercapto-5-methylthio-1,3,4-thiadiazole and 5-carbethoxymethylthio-1,3,4-thiadiazole); pyridine (e.g. 2-methylpyridine and 4-methylpyridine); pyrimidine (e.g. 2-methyl-4-methylthiopyrimidine); quinoline (e.g. 6-methylquinoline, 8-chloroquinoline, 6-fluoroquinoline, 5,6-benzoquinoline and 6,7-benzoquinoline) and imidazolo[4,5-b]quinoxaline;

$n = 0$ or 1,

Y represents hydrogen, halogen, a saturated or unsaturated aliphatic group, an alkoxy group, an alkylthio group or a mercapto group.

The saturated and unsaturated alkyl groups, alkoxy groups and alkylthio groups represented by Y may have, in particular, up to 6 carbon atoms and may be further substituted. Specific examples of saturated or unsaturated alkyl groups represented by Y are methyl, ethyl, alkyl, cyanoalkyl, haloalkyl, alkoxyalkyl and, in particular a methine chain having 1,3, or 5 methine groups, at the end of which chain, in most cases attached through the 2-position, there is an N-alkylated heterocyclic base, of the type known in the chemistry of cyanine dyes. References may be found in F. M. Hamer "The Cyanine Dyes and Related Compounds", (1964), Interscience Publishers John Wiley and Sons. Compounds corresponding to formula I in which Y has the meaning defined above are referred to as "dequaternised cyanine dyes". When such dequaternised cyanine dyes are reacted by the process according to the invention, the products directly obtained from the process are suitable for use as spectral sensitizers without any further reaction.

Specific examples of an alkoxy group represented by Y are carboxyalkoxy groups such as carboxy methoxy. Specific examples of an alkylthio group represented by Y are methylthio and carboxymethylthio.

Suitable hydroxyalkane and hydroxyalkene sulfonic acids are in particular those corresponding to the general formula II $$HO-CH_2-X-SO_3H \qquad (II)$$

in which X represents a substituted or unsubstituted saturated or unsaturated divalent aliphatic hydrocarbon group, preferably one having up to 7 carbon atoms. This hydrocarbon group may be substituted, for example by hydroxyl, halogen, alkoxy or cyano.

The following groups are examples of X:

—$(CH_2)_m$— in which m represents an integer of from 1 to 7, preferably from 1 to 3,

$CH=CH-CH_2-$ and 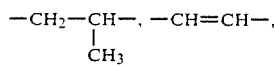

Instead of the free tertiary amine bases, there may also be used their salts with inorganic or organic acids, e.g. the hydrohalides, hydrogen sulfates, p-toluenesulphonates, perfluorobutyrates and acetates.

Metal salts of the sulfonic acids, e.g. their alkaline earth metal salts, may also be used instead of the free sulfonic acids. These salts are preferably reacted with the salts of the tertiary bases.

Hydroxyalkane and hydroxyalkene sulphonates of tertiary amines are also suitable for the reaction according to the invention.

The reactions are generally carried out without solvents although a suitable solvent may be used. Any solvents which are inert in the reaction according to the invention and have a high dissolving power for the reactants are suitable, e.g. phenol or m-cresol, or solvents which form an azeotropic mixture with water, e.g. benzene, toluene, m-xylene, n- or i-butanol, isoamylalcohol, chlorobenzene and anisole.

The reactions according to the invention are accompanied by the elimination of water. This water of reaction is preferably removed from the reaction vessel, for example, by (1) operating under a vacuum,
(2) introducing an anhydrous inert gas, e.g.: nitrogen,
(3) azeotropic distillation with one of the solvents mentioned above or
(4) the presence of a dehydrating agent either in the reaction vessel (e.g. anhydride of an organic acid) or in a receiver attached to the reaction vessel (e.g. $P_4O_{10}$, concentrated sulphuric acid, sodium hydroxide or other dehydrating agent).

Sulfobetaines of tertiary amines prepared by the process according to the invention include in particular those of the following formula III

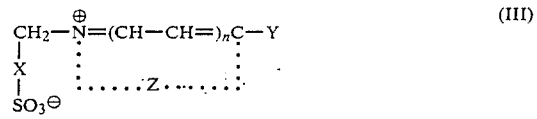

in which n, X, Y and Z have the meanings already specified. These compounds are used for various purposes. For example, they are suitable for use as conductive salts for electroplating. Compounds of the above formula III may also be the end products of a cyanine dye synthesis if Y has the appropriate meaning, i.e. If, as already mentioned above, it represents a methine chain containing 1, 3 or 5 methine groups with a N-alkylated heterocyclic base attached to the end of the chain. Compounds of this type may be used directly for the spectral sensitisation of light-sensitive silver halide emulsions. Generally, the compounds prepared by the process of the invention are also important as intermediate products for the synthesis of polymethine dyes. Thus, for example, the sulfoalkenyl or sulphoalkenyl quaternary salts of heterocyclic bases prepared by the process according to the invention are preferably not isolated but reacted to form polymethine dyes in known manner after the quaternisation reaction without any further purification.

The hydroxyalkane- or hydroxyalkene-sulfonic acids used according to the invention may be prepared by known methods, e.g. by the reaction of a halogen substituted alcohol with an alkali metal sulphite or by chemical addition of bisulphite or sulphur dioxide to a suitable unsaturated alcohol or to an unsaturated aldehyde, followed by reduction. In this way, 3-hydroxy-1-propane sulfonic acid is prepared from allyl alcohol by the chemical addition of sodium bisulphite [J. H. Helberger, Liebigs Ann. Chem. 588, 71 (1954)]. 3-Hydroxy-2-methyl-1-propane sulfonic acid is prepared by the chemical addition of bisulphite to methacrolein followed by reduction with $H_2$/Raney nickel (C. W. Smith et al., J. Amer. Chem. Soc. 75, 748 (1953)). 4-Hydroxy-2-butane-sulfonic acid may be prepared in analogous manner from crotonaldehyde [G. Haubner, Mh. Chemie 12, 541 (1891)]. 4-Hydroxy-1-butane sulfonic acid may be obtained by the reaction of 4-chloro-n-butanol with sulphite (J. H. Helberger, H. Lantermann, Liebigs Ann. Chem. 586, 161 (1954)). 3-Hydroxy-1-propene sulfonic acid may be obtained as a mixture of the cis- and trans-isomers by the chemical addition of bisulfite to propargyl alcohol (German Auslegeschrift No. 1,146,870).

The process according to the invention and its variations are described in more detail in the following Examples.

EXAMPLE 1

Anhydro-2,5,6-trimethyl-3-(3'-sulfobutyl)-benzothiazolium hydroxide.

(a) 3.5 g of 2,5,6-trimethyl-benzothiazole and 3.1 g of 4-hydroxy-2-butane sulfonic acid were heated to 175° C. in an oil bath for 4 hours. After cooling, the reaction product was recrystallised from methanol/isopropanol.
Yield: 2.2 g
Mp: 288°–289° C.
IR Bands: 780, 895, 1040, 1200, 1230, 1450, 1470, 3000, and 3400 cm$^{-1}$.

(b) 3.5 g of 2,5,6-trimethyl-benzothiazole, 3.1 g of 4-hydroxy-2-butane sulfonic acid and 1 g of acetic anhydride were heated to 175° C. in an oil bath for 5 hours. After cooling, the reaction product was recrystallised from methanol.
Yield: 2.4 g
Mp: 288° C.
IR Spectrum identical to that of (a).

EXAMPLE 2

Anhydro-2,5,6-trimethyl-3-(3'-sulfopropyl)-benzothiazolium hydroxide.

(a) 5.3 g of 2,5,6-trimethyl-benzothiazole and 4.2 g of 3-hydroxy-1-propane sulfonic acid were heated to 175° C. in an oil bath for 5 hours. After the first 3 hours, 15 ml of n-butanol were added dropwise and then distilled off as azeotropic mixture with the water formed in the reaction. The quaternary salt produced may be recrystallised from ethanol.
Yield: 4.9 g
Mp: 280° C.
IR Bands: 785, 880, 1040, 1200, 1240, 1345, 1395, 1450, 2900–3000, 3410 cm$^{-1}$.

Similar results were obtained when toluene or chlorobenzene was used instead of n-butanol.

(b) 3.5 g of 2,5,6-trimethyl-benzothiazole, 4.2 g of 3-hydroxy-1-propane sulfonic acid and 1 g of acetic anhydride were heated to 175° C. in an oil bath for 5 hours.
The reaction product was worked up with methanol/isopropanol.
Yield: 5.7 g
Propionic acid anhydride may be used instead of acetic anhydride.

EXAMPLE 3

Anhydro-2,5-dimethyl-3-(3'-sulfopropyl)-benzothiazolium hydroxide.

(a) Obtained from 2/100 mol of 2,5-dimethyl-benzothiazole and 2/100 mol of 3-hydroxy-1-propane sulfonic acid by the method described in example 1b). Yield: 3.7 g, Mp: 253° C.

(b) The same as (a) but using 2/100 mol of 2,5-dimethyl-benzothiazole hydrobromide without acetic anhydride or 1/100 mol of 2,5-dimethyl-benzothiazole and 1/100 mol of 2,5-dimethyl-benzothiazole hydrobromide instead of 2/100 mol of the free base.

(c) From 2/100 mol of 2,5-dimethyl-benzothiazole hydrobromide and 2/100 mol of a 1:1 mixture of sodium and potassium salt of 3-hydroxy-1-propane sulfonate by heating to 180° C. for 1.5 hours and stirring after the mixture has melted.

The preparations obtained according to (a) to (c) were found to have IR-spectra identical to that of a comparison sample prepared from 2,5-dimethyl-benzothiazole and propane sultone.
IR bands: 730, 735, 850, 1040, 1160, 1200, 1225, 1455, 2900–3000, 3410, 3490 cm$^{-1}$.

EXAMPLE 4

Anhydro-2-methyl-3-(3'-sulfopropyl)-benzothiazolium hydroxide.

14.9 g of 2-methyl-benzothiazole and 16 g of 3-hydroxy-1-propane sulfonic acid in 100 ml of anisole were heated to 210° C. (bath temperature) for 5 hours and the reaction mixture was slowly distilled at the same time. The residue was dissolved in alcohol and the solution was clarified with active charcoal and crystallized by the addition of isopropanol.
Yield: 16 g
Mp: 277°–278° C.
IR bands: 790, 1040, 1150, 1170, 1185, 1215, 1240, 1430, 1460, 2850–3100, 3400, 3530 cm$^{-1}$.

EXAMPLE 5

Anhydro-2-methyl-3-(3'-sulfopropyl)-naphtho[1,2-d]-thiazolium hydroxide.

19 g of 3-hydroxy-1-propane sulfonic acid were dissolved in 24 ml of acetic anhydride and left to stand for 20 minutes before 20 g of 2-methyl-naphtho[1,2-d]thiazole were added. After 12 hours heating to 175° C., the reaction product was worked up with methanol.
Yield: 12 g
Mp: 275° C.
IR bands: 735, 760, 780, 850, 880, 1045, 1165, 1210, 1240, 1310, 1520, 2900–3050, 3160, 3420, 3490 cm$^{-1}$.

EXAMPLE 6

Anhydro-2-methyl-5-methoxy-3-(3'-sulfopropyl)-benzoxazolium hydroxide.

8.2 g of 2-methyl-5-methoxybenzoxazole and 8 g of 3-hydroxy-1-propane sulfonic acid were heated to 180° C. for 6 hours while a mixture of 5 ml of acetic anhydride and 50 ml of anisole was slowly added dropwise and the reaction mixture is distilled at the same time. The residue was worked up with acetone and alcohol.
Yield: 6.4 g
Mp: 264°–268° C.
IR bands: 790, 830, 960, 1010, 1040, 1200, 1235, 1310, 1405, 1450, 1480, 1500, 1590, 1615, 2900–3050, 3400 cm$^{-1}$.

EXAMPLE 7

Anhydro-2-methyl-5-phenyl-3-(3'-sulfopropyl)-benzoxazolium hydroxide.
Prepared from:

10.5 g of 2-methyl-5-phenyl-benzoxazole and
8 g of 3-hydroxy-1-propane sulfonic acid by the method described in Example 6.
Yield: 12.4 g
Mp: 282° C.
IR bands: 705, 780, 1040, 1200, 1410, 1475, 1600, 2900–3050, 3300–3400, 3600 cm$^{-1}$.

EXAMPLE 8

Anhydro-2-methyl-3-(3'-sulfopropyl)-naphtho[1,2-d]-oxazolium hydroxide.

10.5 g of 2-methylnaphtho[1,2-d]oxazole.

8 g of 3-hydroxy-1-propane sulfonic acid in 5 ml of acetic anhydride and 50 ml of anisole were heated to 180° C. for 6 hours under conditions of distillation while a dry stream of nitrogen was passed through the reaction mixture.
Yield: 6.7 g
Mp: 271°–272° C.
IR Bands: 730, 780, 825, 1040, 1175, 1200, 1375, 1410, 1480, 1540, 1575, 2900–3100, ~3400 cm$^{-1}$.

EXAMPLE 9

Anhydro-2-methyl-3-(3'-sulfopropyl)-6-methoxybenzoxazolium hydroxide.

Prepared from 2-methyl-6-methoxy-benzoxazole by a method similar to that of Example 6. Mp: 277° C.

IR bands: 765, 780, 795, 820, 850, 1015, 1040, 1110, 1200, 1350, 1445, 1505, 1595, 3000 cm$^{-1}$.

EXAMPLE 10

Anhydro-2-methyl-3-(3'-sulfopropyl)-benzoxazolium hydroxide.

Prepared from 7 ml of 2-methyl-benzoxazole and 8 g of 3-hydroxy-1-propane sulfonic acid by a method similar to that of Example 6. The reaction product was worked up with isopropanol and acetone.
Yield: 5.2 g
Mp: 138°–142° C.
IR Bands: 785, 920, 1035, 1175, 1190, 1220, 1240, 1465, 1600, 2900–3100, 3400, 3530 cm$^{-1}$.

Similar results were obtained when 4-chlorotoluene was used as solvent instead of anisole.

EXAMPLE 11

Anhydro-2-methyl-3-(3'-sulfopropyl)-benzoselenazolium hydroxide.

2 g of 2-methyl-benzoselenazole, 1.4 g of 3-hydroxy-1-propane sulfonic acid and 0.5 ml of acetic anhydride were heated to 175° C. in an oil bath for 4 hours. The reaction product was worked up with methanol/ethanol.
Yield: 1.6 g
Mp: 267°–268° C. (after recrystallization from ethanol, Mp: 274° C.).

Slightly lower yields are obtained in the absence of acetic anhydride.

EXAMPLE 12

Anhydro-2,5-dimethyl-6-methoxy-3-(3'-sulfopropyl)-benzoselenazolium hydroxide.

A mixture of 4.8 g of 3-hydroxy-1-propane sulfonic acid, 1.5 ml of acetic anhydride and 7.2 g of 2,5-dimethyl-6-methoxybenzoselenazole were heated to 175° C. for 4 hours while a dry stream of nitrogen was passed through. The reaction product was crystallized from alcohol and then from methanol.
Yield: 5.3 g
Decomposition at 310° C.
IR bands: 770, 785, 810, 880, 910, 1040, 1200, 1270, 1415, 1440, 1490, 1525, 1580, 1610, 2910, 3010, 3400 cm$^{-1}$.

EXAMPLE 13

Anhydro-2-methyl-5-methoxy-3-(3'-sulfopropyl)-benzoselenazolium hydroxide.

Prepared from 2-methyl-5-methoxy-benzoselenazole and 3-hydroxy-1-propane sulfonic acid by a method similar to that of Example 12.
Mp: 300° C.
IR bands: 800, 825, 840, 845, 1040, 1140, 1200, 1240, 1350, 1450, 1470, 1605, 2900–3070, 3400 cm$^{-1}$.

EXAMPLE 14

Anhydro-1,2-dimethyl-5,6-dichloro-3-(3'-sulfopropyl)-benzimidazolium hydroxide.

Prepared from 4.3 g of 1,2-dimethyl-5,6-dichlorobenzimidazole and 2.8 g of 3-hydroxy-1-propane sulfonic acid by 4 hours heating to 175° C. and crystallization with isopropanol.
Yield: 4.5 g
Mp: 352°–355° C.
IR bands: 720, 900, 1030, 1040, 1115, 1165, 1185, 1205, 1420, 1480, 1540, 3010, 3400 cm$^{-1}$.

EXAMPLE 15

Anhydro-1-ethyl-2-methyl-5,6-dichloro-3-(3'-sulfopropyl)-benzimidazolium hydroxide.

Prepared from 1-ethyl-2-methyl-5,6-dichlorobenzimidazole by a method similar to that of Example 14.
Yield: 43%
Mp: 315°–318° C.
IR bands: 1045, 1110, 1200, 1415, 1470, 1525, 2990, 3400 cm$^{-1}$.

EXAMPLE 16

Anhydro-1,2-dimethyl-5-pyrrolidino-sulfonyl-3-(3'-sulphopropyl)-benzimidazolium hydroxide.

Prepared from 5.6 g of 1,2-dimethyl-5-pyrrolidinosulfonyl-benzimidazole by 3 hours heating to 185° C. by a method similar to that of Example 14.
Yield: 6.7 g
Mp: 332° C. (from water)
IR bands: 660, 1040, 1160, 1205, 1220, 1335, 1370, 1450, 1485, 3020, 3380 cm$^{-1}$.

EXAMPLE 17

Anhydro-1-(3'-sulfopropyl)-quinolinium hydroxide. Prepared by reacting quinoline and 3-hydroxy-1-propane sulfonic acid for 8 hours by a method similar to that of Example 14. Mp: 290°–291° C.

IR bands: 790, 830, 1050, 1170- 1210, 1240, 1270, 1380, 1535, 1590, 1630, 2960–3070, 3420 cm$^{-1}$.

EXAMPLE 18

Anhydro-2-(3'-sulfopropyl)-isoquinolinium hydroxide. Similarly to Example 17 from isoquinoline, Mp: 314°–315° C.

IR bands: 730, 760, 795, 840, 1040, 1200, 1290, 1400, 1640, 3010, 3060, 3400–3500 cm$^{-1}$.

EXAMPLE 19

Anhydro-1-(3'-sulfopropyl)-2-methyl-quinolinium hydroxide.

Similarly to Example 17 from quinaldine by 10 hours heating to 200° C.

Mp: 284° C.

IR bands: 730, 785, 840, 1040, 1155, 1200, 1370, 1525, 1600, 1620, 3070, ∼3400 cm$^{-1}$.

EXAMPLE 20

Anhydro-1-(3'-sulfopropyl)-pyridinium hydroxide. Prepared similarly to Example 14 from 2 g of pyridine and 3 g of 3-hydroxy-1-propane sulfonic acid by heating to 175° C. for 6 hours and crystallizing from methanol.

Yield: 3.1 g

Mp: 278° C.

IR bands: 695, 775, 790, 1040, 1145, 1170, 1200, 1220, 1240, 1470, 1490, 1505, 1630, 2940, 3010–3100, 3400 cm$^{-1}$.

EXAMPLE 21

Anhydro-2-methyl-3-(3'-sulfobutyl)-benzothiazolium hydroxide.

Similarly to Example 14 from 3 g of 2-methyl-benzothiazole and 3.4 g of 4-hydroxy-2-butane sulfonic acid by heating to 175° C. for 4 hours.

Yield: 2.2 g

Mp: 277°–278° C.

IR bands: 770, 790, 1030, 1170, 1200, 1340, 1380, 1440, 1460, 1475, 1515, 1575, 1640, 2910–3070, 3430, 3480 cm$^{-1}$.

EXAMPLE 22

Anhydro-2,5-dimethyl-3-(3'-sulfobutyl)-benzoselenazolium hydroxide.

Similarly to Example 21 from 0.03 mol of 2,5-dimethylbenzoselenazole in 1 hour, working up with isopropanol/acetone.

Yield: 2.2 g

Mp: 285° C. (methanol).

IR bands: 790, 830, 1040, 1190, 1280, 1440, 1460, 1650, ∼2930, ∼3450 cm$^{-1}$.

EXAMPLE 23

Anhydro-2-methyl-3-(3'-sulfobutyl)-benzoselenazolium hydroxide.

Similarly to Example 22 from 2-methyl-benzoselenazole and 4-hydroxy-2-butane sulfonic acid by heating for 80 minutes at 150° C. and 30 minutes at 175° C. and working up the reaction melt with isopropanol and acetone.

Mp: 290° C. (methanol)

IR bands: 780, 1035, 1175, 1205, 1440, 2940, 3060, 3400 cm$^{-1}$.

EXAMPLE 24

Anhydro-2,5-dimethyl-3-(3'-sulfobutyl)-6-methoxybenzoselenazolium hydroxide.

Similarly to Example 21 from 0.01 mol of 2,5-dimethyl-6-methoxy-benzoselenazole by heating to 175° C. for 1 hour. Crystallized from isopropanol/methanol.

Yield: 0.9 g

Mp: 295° C.

IR bands: 780, 1035, 1185, 1200, 1260, 1440, 1470, 1490, 1520, 1605, 2850–3100, 3400 cm$^{-1}$.

EXAMPLE 25

Anhydro-2,5-dimethyl-3-(3'-sulfo-2'-propen-1'-yl)-benzothiazolium hydroxide.

Similarly to Example (2b) from 2,5-dimethyl-benzothiazole and 3-hydroxy-1-propene sulfonic acid, Mp: 280°–282° C.

EXAMPLE 26

Anhydro-2,6-dimethyl-3-(3'-sulfo-2'-propen-1'-yl)-benzothiazolium hydroxide.

Similarly to Example 25 from 2,6-dimethyl-benzothiazole,

Mp: 223°–225° C.

EXAMPLE 27

Anhydro-2,5-dimethyl-3-(3'-sulfo-2'-propen-1-yl)-benzoselenazolium hydroxide.

Similarly to Example (2b) from 2,5-dimethyl-benzoselenazole and 3-hydroxy-1-propene sulfonic acid, decomposition at 286° C.

EXAMPLE 28

Anhydro-2,5-dimethyl-3-(3'-sulfo-2'-chloropropyl)-benzoselenazolium hydroxide.

Similarly to Example (2b) from 2,5-dimethyl-benzoselenazole and 3-hydroxy-2-chloro-1-propane sulfonic acid, decomposition at 245°–246° C.

EXAMPLE 29

Anhydro-3-ethyl-3'-(3-sulfobutyl)-9-methyl-thiacarbocyanine hydroxide.

14.9 g of 2-methyl-benzothiazole and 17.2 g of 4-hydroxy-2-butane sulfonic acid in 50 ml of anisole were heated to 200° C. (bath temperature) for 3 hours. A mixture of water and anisole distilled off. The residue freed from anisole was heated gently with 28.9 g of 2-(2-methylthio-1-propenyl)-3-ethyl-benzothiazolium methyl sulfate in 120 ml of ethanol. After the addition of 24 ml of triethylamine at 40° C., leaving to stand at room temperature for 3 hours and cooling with ice for 2 hours, the resulting dye was suction filtered, washed with methanol and recrystallized from a 1:3 mixture of chloroform and methanol.

Yield: 25.5 g, Absorption maximum 544 nm (log ε=5.07).

EXAMPLE 30

Sodium salt of anhydro-5,5'-diphenyl-3,3'-bis-(3-sulfobutyl)-9-ethyl-oxacarbocyanine hydroxide.

12 g of 2-methyl-5-phenyl-benzoxazole and 10.2 g of 4-hydroxy-2-butane sulfonic acid were heated to 200° C. for 20 minutes and then for a further 20 minutes after the addition of 3 ml of acetic anhydride. The reaction product was taken up in 15 ml of m-cresol and converted into the dye by reaction with 15 ml of orthopropionic acid triethyl ester in the presence of 15 ml of triethylamine (40 minutes steam bath). After the m-cresol had been washed out with ethyl acetate, the dye was converted into its sodium salt with aqueous sodium chloride solution (30 minutes steam bath) and recrystallized from methanol/chloroform.

Yield: 2.4 g, absorption maximum 503 nm (log ε=5.18).

EXAMPLE 31

Sodium salt of 3-ethyl-5-[3-(3-sulfobutyl)-5-methylthio-1,3,4-thiadiazolin-2-ylidene]-rhodanine.

8.9 g of 2,5-bis-methylthio-1,3,4-thiadiazole and 8.6 g of 4-hydroxy-2-butane sulphonic acid in 35 ml of anisole were heated to 200° C. for 1 hour. A mixture of water and anisole distilled off. The syrupy residue was washed with acetone and, after the addition of 3.5 g of N-ethyl rhodanine, it was dissolved in 25 ml of ethanol. After the addition of 5 ml of triethylamine at 40° C., the reaction mixture was left to stand for a further 2.5 hours and the resulting dye solution was then poured into 250 ml of water. After filtration, the dye was isolated by precipitation with saturated sodium chloride solution and suction filtration.

Yield: 1.9 g, absorption maximum 421 nm (log $\epsilon=4.63$).

EXAMPLE 32

Anhydro-3-(3'-sulfopropyl)-4,5-dimethyl-thiazolium hydroxide.

Similarly to Example 14 from 6 g of 4,5-dimethyl thiazole and 8 g of 3-hydroxy-1-propane sulfonic acid, by 5 hours heating at 175° C. The product was worked up with acetone.

Yield: 3.4 g, Mp: 174°–175° C. (methanol/isopropanol).

IR bands: 750, 800, 870, 1035, 1200, 1450, 1590, 2990, 3400 cm$^{-1}$.

EXAMPLE 33

Anhydro-3-methyl-3'-(3-sulfopropyl)-thia-2'-carbocyanine hydroxide.

2.9 g of quinaldine, 3 g of 3-hydroxy-1-propane sulfonic acid and 2 ml of acetic anhydride were heated to 200° C. (bath temperature) for 10 hours. The residue was taken up with 40 ml of methanol and was then boiled on a steam bath for 5 minutes after the addition of 8 g of 2-(2-acetanilido-vinyl)-3-methyl-benzothiazolium perchlorate and 3 ml of triethylamine. The resulting dye was boiled with water and recrystallized from chloroform/methanol.

Yield: 3.4 g,
Mp: 288° C., absorption maximum 586 nm (log $\epsilon=5.08$).

EXAMPLE 34

Potassium salt of anhydro-5,5',9-trimethyl-3,3'-bis(3-sulfopropyl)-thiacarbocyanine hydroxide.

7.4 g of 2,5-dimethyl-benzothiazole hydrobromide and 6.1 g of potassium 3-hydroxy-propane sulfonate were heated to 180° C. for 1.5 hours.

The reaction mixture was then dissolved in m-cresol and converted into the dye by reaction with triethyl ortho-acetate and triethylamine at 60° C. The dye was converted into its potassium salt with potassium acetate and recrystallized from methanol.

Yield: 4.5 g, Mp: 298°–302° C., absorption maximum 548 nm (log $\epsilon=5.08$).

EXAMPLE 35

Anhydro-3-ethyl-9-methyl-3'-(2-sulfoethyl)-thiacarbocyanine hydroxide.

2.3 g of 2-methyl-benzothiazole hydrobromide and 1.5 g of sodium 2-hydroxy ethane sulfonate were heated to 220° C. for 1 hour. The reaction mixture was taken up with methanol and to it were added 3.8 g of 3-ethyl-2-(2-methylthio-1-propenyl)-benzothiazolium methyl sulfate. The dye crystallized after the addition of 2 ml of triethylamine and 5 minutes heating on the steam bath.
Mp: 295°–296° C., absorption maximum 541 nm.

EXAMPLE 36

Sodium salt of 1,3-dimethyl-2-thio-5-[2-(6-methoxy-3-sulfopropyl-benzoxazolin-2-ylidene)-ethylidene]-hydantoin 1.4 g of 3-hydroxy propane sulfonic acid were mixed with 0.5 ml of acetic anhydride and, after the addition of 1.6 g of 6-methoxy-2-methyl-benzoxazole, the mixture was heated to 180° C. for 4 hours. After cooling to 70° C., 3 g of diphenyl formamidine were added and the reaction mixture was heated to 130° C. for 60 minutes. After cooling to 80° C., the reaction mixture was washed with ethyl acetate and the insoluble reaction product was taken up with 15 ml of ethanol. After the addition of 1.4 g of 1,3-dimethyl-2-thiohydantoin, 3 ml of triethylamine and 0.5 ml of acetic anhydride, the reaction mixture was stirred on a steam bath for 5 minutes and then left to stand at room temperature for 1 hour. The dye was precipitated with methanolic NaClO$_4$ solution.

Yield: 0.5 g,
Mp: 328°–332° C., absorption maximum: 492 nm.

EXAMPLE 37

Potassium 5-methyl-2-acetylmethylene-3-(3-sulfonato-2-propen-1-yl)-benzothiazoline.

52 g of 2,5-dimethyl-benzothiazole hydrobromide and 48 g of potassium 3-hydroxy-1-propensulphonate were heated to 140° C. for 1 hour. 90 ml of acetic anhydride and 32 ml of triethylamine were added to the resulting melt of the quaternary salt and the mixture was stirred at 100° C. for 1 hour. The acetic acid formed in the reaction was then distilled off and the residue was taken up with water. Hydrochloric acid was added, whereupon the intermediate product crystallized.

Yield: 27 g,
Mp: 245°–248° C.

The intermediate product can be converted in known manner by stepwise reaction e.g. with (1) P$_2$S$_5$, (2) dimethyl sulfate and (3a) a heterocyclic methyl quaternary salt into a symmetric or asymmetric carbocyanine or (3b) a heterocyclic ketomethylene compound into a dimethine merocyanine.

EXAMPLE 38

Anhyro-5-phenyl-3-(3-sulphopropyl)-3'-methyl-oxathiacarbocyanine hydroxide.

1/100 ml of 5-phenyl-2-methyl-benzoxazole and 1/100 mol of 3-hydroxy propane sulfonic acid were heated to 175° C. for 5 hours with the addition of 1/200 mol of acetic anhydride. 1/100 mol of 2-β-phenylimino-ethylidene-3-methyl-benzothiazoline, 10 ml of ethanol, 3 ml of triethylamine and 1 ml of acetic anhydride were added to the resulting melt when cold. The formation of dye was completed by heating the reaction mixture on a steam bath. Absorption maximum: 524 nm.

EXAMPLE 39

Anhydro-3-(3-sulfobutyl)-5'-chloro-3'-ethyl-oxathiacarbocyanine hydroxide.

Similarly to Example 38 from 2-methyl-benzoxazole, 4-hydroxy-2-butane sulfonic acid and 2-β-phenylimino-ethylidene-3-ethyl-5-chlorobenzothiazoline. Absorption maximum: 523 nm.

EXAMPLE 40

Anhydro-5-methyl-3-(4-sulfobutyl)-5'-phenyl-3'-ethylthiaoxacarbocyanine hydroxide.

1/100 mol of 2,5-dimethyl-benzothiazole hydrobromide were reacted by heating for 5 hours with 1/100 mol of 4-hydroxy-1-butane sulfonic acid. The reaction mixture was taken up with 15 ml of ethanol and after the addition of 1/100 mol of 2-acetanilido vinyl-3-ethyl-5-phenyl-benzoxazoliumiodide and 3 ml of triethylamine the dye was formed by boiling of the reaction mixture for 15 minutes.

Absorption maximum: 526 nm.

EXAMPLE 41

Anhydro-5,5',6-trimethyl-3-(3-sulfopropyl)-3',9-diethylthiacarbocyanine hydroxide.

2.6 g of 2,5,6-trimethyl-benzothiazole hydrobromide and 1.9 g of K-3-hydroxy-1-propane sulfonate were heated to 175° C. for 3 hours while a stream of anhydrous nitrogen was passed through. When the reaction product had cooled, it was taken up with methanol, filtered from potassium bromide and then heated on a steam bath for 25 minutes after the addition of a methanolic solution of 3.4 g of 3-ethyl-2-(2-methoxy-1-butenyl)-5-methyl-benzothiazolium methyl sulfate and 2.9 ml of triethylamine. The dye which crystallized was recrystallized from methanol/chloroform.

Yield: 2.5 g, Mp: 295°–296° C., absorption maximum: 557 nm (log $\epsilon = 5.08$).

EXAMPLE 42

Anhydro-2-(2-anilinovinyl)-3-(3-sulfopropyl)-5-chlorobenzoxazolium hydroxide.

8.5 g of 2-methyl-5-chlorobenzoxazole and 8 g of 3-hydroxy-1-propane sulfonic acid were heated to 180° C. A mixture of 5 ml of acetic anhydride and 50 ml of anisole was then added dropwise over a period of 3 hours while a stream of anhydrous nitrogen was passed through and the reaction mixture was distilled at the same time. Heating was then continued for 1 more hour at 180° C. The residue was taken up with 12 ml of ethanol and after the addition of 9.2 g of the triethyl ester of ortho formic acid and 5.8 g of aniline it was boiled for 5 hours.

Yield: 7.2 g,

Mp: 311°–312° C. (decomposition, hydroxy propionitrile).

IR bands: 695, 735, 790, 820, 845, 885, 970, 1040, 1180, 1215, 1255, 1300, 1335, 1350, 1375, 1480, 1500, 1590, 1610, 1635, 1660, 2860–3160, 3500 cm$^{-1}$.

EXAMPLE 43

Anhydro-2-(2-anilinovinyl)-3-(3-sulfopropyl)-benzoxazolium hydroxide.

Prepared similarly to Example 42 from 2-methyl-benzoxazole (7 g), Yield: 5.7 g, Mp: 325°–327° C. (decomposition).

IR bands: 695, 745, 765, 790, 880, 970, 1040, 1180, 1190, 1210, 1260, 1300, 1330, 1380, 1405, 1480, 1500, 1590, 1615, 1660, 2860–3160, ~3400 cm$^{-1}$

EXAMPLE 44

Sodium salt of 5-[3-(3-sulfobutyl)-benzothiazolinylidene]-3-ethyl-rhodanine.

18 g of 2-methyl-thiobenzothiazole and 17.2 g of 4-hydroxy-2-butane sulfonic acid in 35 ml of anisole were heated to 200° C. for 2 hours under distillation conditions.

The residue was washed with ether after cooling and then taken up with 150 ml of ethanol. 13.5 g of 3-ethyl-rhodanine and 10 ml of triethylamine were added. After 1 hour at room temperature and filtration, the solution was poured into 140 ml of water and the dye was precipitated with saturated sodium chloride solution.

Yield: 3.4 g absorption maximum: 429 nm (log $\epsilon = 4.78$).

EXAMPLE 45

Anhydro-3-(3-sulfopropyl)-3'-methyl-thiacyanine hydroxide. 1.7 g of 2-mercapto benzothiazole and 3 g of 3-hydroxy-1-propane sulfonic acid in 3 ml of m-cresol were heated to 175° C. for from 7 to 8 hours. After cooling, 3.3 g of 2,3-dimethyl-benzothiazolium-p-tolylate, 30 ml of absolute ethanol and 5 ml of triethylamine were added. The reaction mixture was then heated to 50° C. and left to stand for 1 hour. The dye which crystallized was removed by suction filtration.

Yield: 1.5 g, Mp: >320° C., absorption maximum 522 nm (log $\epsilon = 4.90$).

EXAMPLE 46

3-ethyl-5-[1-methyl-3-(3-sulfopropyl)-5,6-dichlorobenzimidazolin-2-ylidene]-rhodanine; triethylamine salt:

(a) 4.7 g of 1-methyl-2-mercapto-5,6-dichlorobenzimidazole, 6 g of 3-hydroxy-1-propane sulfonic acid and 4 g of phenol heated to 175° C. for 8 hours. The reaction product is dissolved in 40 ml of hot ethanol and filtered. 4 g of 3-ethyl rhodanine and 5 ml of triethylamine were added. The reaction mixture was left to stand for 2 hours and then suction filtered.

Yield: 4.1 g, Mp: 228°–230° C. (ethanol/methanol). Absorption maximum: 423 nm (log $\epsilon = 4.67$).

(b) The same as (a) from 2.3 g of 1-methyl-2-mercapto-5,6-dichlorobenzimidazole and 6 g of 3-hydroxy-1-propane sulfonic acid, but without the addition of phenol.

Yield: 1.9 g, Mp: 227°–229° C.

EXAMPLE 47

Anhydro-2-methyl-3-(3'-sulfopropyl)-4,5-diphenyloxazolium hydroxide.

Similarly to Example 6 from 9 g of 2-methyl-4,5-diphenyloxazole and 6 g of 3-hydroxy-1-propane sulfonic acid; worked up with ethyl acetate and i-propanol.

Yield: 4.9 g, Mp: 272°–275° C.

IR bands: 695, 720, 765, 1045, 1210, 1450, 1700, 2900–3040, ~3400 cm$^{-1}$.

EXAMPLE 48

Anhydro-3-(3-sulfopropyl)-3'-ethyl-thiocarbocyanine hydroxide.

Similarly to Example 1 from 2-(3-ethyl-2-benzothiazolinylidene)-1-propenyl]-benzothiazole and 3-hydroxy-1-propane sulfonic acid. Mp: 244°–247° C., absorption maximum: 557 nm.

We claim:

1. The process for the preparation of a compound of the following formula III

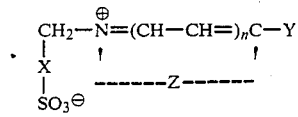

in which

X represents a bivalent group selected from the following:

—$(CH_2)_m$— in which m is an integer from 1 to

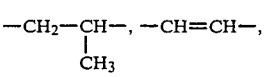

-continued

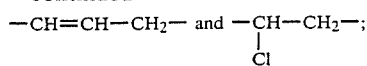

Z represents the atoms required for completing a heterocyclic group comprising at least one 5-membered or 6-membered heterocyclic ring which may have a benzene or naphthalene ring condensed to it, said heterocyclic ring being selected from the group consisting of pyrroline, oxazoline, thiazoline, selenazoline, imidazole, oxazole, thiazole, selenazole, 1,3,4-thiadiazole and pyridine n=0 or 1, Y represents halogen, an unsaturated aliphatic group having up to 6 carbon atoms, an alkoxy group having up to 6 carbon atoms or mercapto, or when Z completes a heterocyclic group comprising at least one pyrroline, oxazoline, thiazoline, selenazoline, 1,3,4-thiadiazole, pyridine or condensed naphthalene ring, Y may also be selected from the group consisting of hydrogen, methyl and ethyl, in which process a heterocyclic base of the following formula I

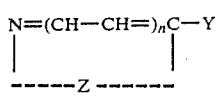

wherein Y, Z and n have the meanings already specified or a salt of such a base with an inorganic or organic acid is reacted with a hydroxyalkane sulfonic acid of a hydroxyalkene sulfonic acid corresponding to formula II

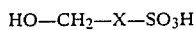

in which X has the meaning already specified or with a metal salt or this acid at a temperature between 140° and 200° C. and water of reaction is removed from the reaction mixture.

2. The process as claimed in claim 1, in which the reaction is carried out in the presence of a solvent which forms an azeotropic mixture with water.

3. The process as claimed in claim 1, in which the reaction is carried out in the presence of phenol.

4. The process as claimed in claim 1, in which the reaction is carried out in the presence of an anhydride of an organic acid.

5. The process for the preparation of a compound of the following formula III

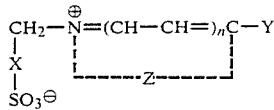

in which

X represents a bivalent group selected from the following:

—(CH$_2$)$_m$— in which m is an integer from 1 to 3,

—CH$_2$—CH—, —CH=CH—,
      |
      CH$_3$

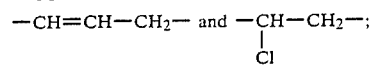

Z represents the atoms required for completing a heterocyclic group selected from the group consisting of pyridine, quinoline and isoquinoline n=0 or 1, Y represents an alkylthio group having up to 6 carbon atoms or methyl, in which process a heterocyclic base of the following formula I

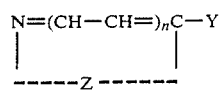

wherein Y, Z and n have the meanings already specified or a salt of such a base with an inorganic or organic acid is reacted with a hydroxyalkane sulfonic acid or a hydroxyalkene sulfonic acid corresponding to formula II

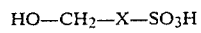

in which X has the meaning already specified or with a metal salt of this acid at a temperature between 140° and 200° C. and water of reaction is removed from the reaction mixture.

6. The process for the preparation of a compound of the following formula III

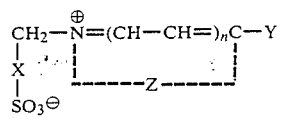

in which

X represents a bivalent group selected from the following: —(CH$_2$)$_m$— in which m is an integer from 1 to 3,

—CH$_2$—CH—, —CH=CH—,
      |
      CH$_3$

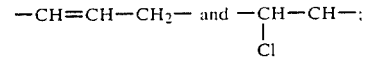

Z represents the atoms required for completing a heterocyclic group selected from the group consisting of pyrroline, oxazoline, thiazoline, selenazoline, n=0, Y represents an alkylthio group having up to 6 carbon atoms, in which process a heterocyclic base of the following formula I

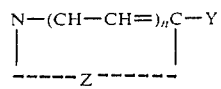

wherein Y, Z and n have the meanings already specified or a salt of such a base with an inorganic or organic acid is reacted with a hydroxyalkane sulfonic acid or a hydroxyalkene sulfonic acid corresponding to formula II $$HO-CH_2-X-SO_3H \quad \text{(II)}$$

in which X has the meaning already specified or with a metal salt of this acid at a temperature between 140° and 200° C. and water of reaction is removed from the reaction mixture.

7. The process for the preparation of a compound of the following formula III $$\begin{array}{c} \overset{\oplus}{\underset{|}{CH_2-N}}=(CH-CH=)_nC-Y \\ \underset{|}{X} \qquad \qquad \overset{|}{\text{------Z------}} \\ SO_3^{\ominus} \end{array} \quad \text{(III)}$$

in which

X represents a bivalent group selected from the following: $-(CH_2)_m-$ in which m is an integer from 1 to 3, $$-CH_2-\underset{\underset{CH_3}{|}}{CH}-, \ -CH=CH-,$$

-continued
$$-CH=CH-CH_2- \text{ and } -\underset{\underset{Cl}{|}}{CH}-CH_2-;$$

Z represents the atoms required for completing a heterocyclic group selected from naphthoxazole, naphthothiazole, naphthoselenazole and naphthimidazole, n=0, Y represents alkylthio group having up to 6 carbon atoms, in which process a heterocyclic base of the following formula I $$\begin{array}{c} N=(CH-CH=)_nC-Y \\ | \qquad \qquad | \\ \text{-----Z------} \end{array} \quad \text{(I)}$$

wherein Y, Z and n have the meanings already specified or a salt of such a base with an inorganic or organic acid is reacted with a hydroxyalkane sulfonic acid or a hydroxyalkene sulfonic acid corresponding to formula II $$HO-CH_2-X-SO_3H \quad \text{(II)}$$

in which X has the meaning already specified or with a metal salt of this acid at a temperature between 140° and 200° C. and water of reaction is removed from the reaction mixture.

* * * * *